United States Patent [19]

Sugiyama et al.

[11] Patent Number: 4,643,939
[45] Date of Patent: Feb. 17, 1987

[54] OIL ABSORBING COSMETIC TISSUE

[75] Inventors: Yasuo Sugiyama; Osamu Hiraoka, both of Osaka; Tamotsu Nakazawa, Tokyo; Kenji Nakamura, Osaka, all of Japan

[73] Assignees: Shiseido Company Ltd., Tokyo; Nakamura Bussan Kabushiki Kaisha, Osaka, both of Japan

[21] Appl. No.: 835,928

[22] Filed: Mar. 4, 1986

[51] Int. Cl.$^4$ .............................................. B32B 5/16
[52] U.S. Cl. .................................... 428/283; 424/27; 424/28; 428/402; 428/913; 604/360
[58] Field of Search ................... 424/27, 28; 604/360; 428/913, 283, 907, 537, 402

[56] References Cited

U.S. PATENT DOCUMENTS 2,961,373 11/1960 Boyer ................................ 424/27
4,035,506 7/1977 Lucas et al. ...................... 260/399

FOREIGN PATENT DOCUMENTS 1196407 6/1970 United Kingdom ................ 424/27

Primary Examiner—James J. Bell
Attorney, Agent, or Firm—Sprung, Horn, Kramer & Woods

[57] ABSTRACT

An oil absorbing cosmetic tissue consisting of an oil absorbant sheet impregnated with a bactericide, the tissue thus able to remove excess skin oil and at the same time suppress the proliferation of bacteria so as to reduce the adverse effects of bacteria on the skin.

12 Claims, 2 Drawing Figures

OIL ABSORBING COSMETIC TISSUE

BACKGROUND OF THE INVENTION

1. Field of the Invention

The present invention relates to an oil absorbing tissue for cosmetic use. More particularly, it relates to an oil absorbing cosmetic tissue for absorbing facial oil before application of makeup.

2. Description of the Related Art

Considerable skin oil is discharged from the face, particularly around the nose, chin, and between the eyebrows. This makes those areas oily and can easily ruin the makeup applied thereon.

When makeup is applied on the skin with the oil still present, the makeup does not take to the skin well. It is therefore better in view of the cosmetic effect to apply the makeup only after removing the oil.

For this reason, the general practice when applying makeup is to first press or wipe the oily portion of the face with oil absorbing cosmetic tissue to remove oil. Various cosmetic tissues have been marketed for this purpose. The commercially available oil absorbing cosmetic tissues are generally comprised of plant fibers having an oil absorbing property. For example, hemp fibers have an excellent oil absorbing property.

To enhance marketability, it is not only necessary that the cosmetic tissue absorb the oil, but also that the user can visually confirm that the oil is absorbed. To facilitate confirmation of the oil absorbing effect, it has been proposed in Japanese Examined Patent Publication (Kokoku) No. 56-8606 to mix transparent synthetic resin fibers together with the nontransparent oil absorbing plant fibers so that, when the oil is absorbed, the relevant portion of the tissue becomes transparent. Oil absorbing cosmetic tissue of that type has already been marketed. It has also been proposed to coat the surface of the oil absorbing cosmetic tissue with silica, talc, and other inorganic powder.

As seen above, in the past, the emphasis on an oil absorbing cosmetic tissue has been on improvements in the oil absorbing property and the confirmability of the oil absorbing effect.

Besides the oil, however, there is a large amount of bacteria present on the skin. These bacteria normally do not have any detrimental effect on the skin, but when skin oil accumulates due to enlargement or proliferation of sebaceous glands or corneousness of hair follicle pores, acne bacillus, skin staphyloccus, and the like proliferate, and decompose the triglycerides among the oil components from the skin. Thus, the triglycerides are converted to free fatty acids.

Triglycerides themselves do not afford an adverse effect on the skin, but the free fatty acids formed by the decomposition of the triglycerides due to the bacteria damage the cells forming the skin, inducing inflammation. In actuality, according to "Keshohin Gaku" (Cosmetics) (Tetsusaku Ikeda, published Mar. 1, 1983 from Nanzando), it has been found that the oil of acne-ridden skin contains a large amount of free fatty acids and little triglycerides. Therefore, while the bacteria is not a direct cause of acne, it does aggravate small pimples and create acne along with inflammation.

While, as mentioned above, improvements have been made to oil absorbing cosmetic tissue with respect to the oil absorbing property itself and to the confirmability of the oil absorbing effect, nothing has been done to positively suppress the proliferation of bacteria so as to reduce the adverse effect of bacteria on the skin.

SUMMARY OF THE INVENTION

An object of the present invention is to provide an oil absorbing cosmetic tissue which can both remove excess skin oil and at the same time suppress the proliferation of bacteria so as to reduce the adverse effect of bacteria on the skin.

Other objects and advantages of the present invention will be apparent from the following description.

In accordance with the present invention, there is provided an oil absorbing cosmetic tissue comprised of an oil absorbing sheet which contains a bactericide.

BRIEF EXPLANATION OF THE DRAWINGS

These and other objects of the present invention will become more apparent from the ensuing description of the preferred embodiments with reference to the accompanying figures, in which.

DESCRIPTION OF THE PREFERRED EMBODIMENTS

Figure 1:
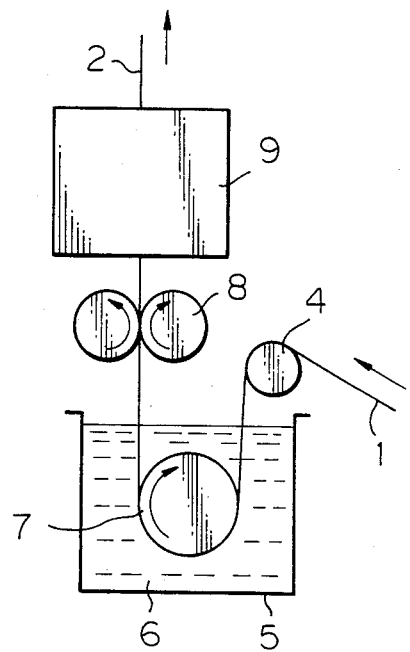
FIG. 1 is a schematic front view of an embodiment of an apparatus for manufacturing the oil absorbing cosmetic tissue of the present invention.
Figure 2:
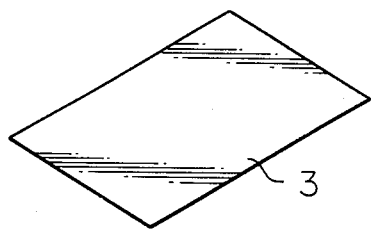
FIG. 2 is a perspective view of the oil absorbing cosmetic tissue of the present invention.

The oil absorbing cosmetic tissue of the present invention is comprised of a sheet having the ability to absorb skin oil. Any sheet used for conventional oil absorbing cosmetic tissue may be used in the present invention. For example, sheets comprised of hemp fiber or other plant fiber alone or mixtures of plant fiber and synthetic resin fibers or of sheets of the same with surfaces coated with silica, talc, and other inorganic powder may be used in the present invention.

The bactericide contained in the tissue proper may be any bactericide conventionally used in cosmetics, for example, phenol, p-chlorometacresol, resorcin, p-oxybenzoate, benzoic acid and its salts, salicylic acid and its salts, dehydroacetic acid and its salts, sorbic acid and its salts, boric acid, hexachlorophene, tetramethylthiuram disulfide, sulfur, carbanilide bactericides, and triclosan.

When the bactericide is incorporated into the oil absorbing cosmetic tissue base, immersion or coating may be used in the present invention.

In the case of immersion, the bactericide is dissolved in water, alcohol, a mixture of water and alcohol, or other appropriate solutions. The sheets of the oil absorbing cosmetic tissue are immersed in the solution, wrung out, and then dried.

In the case of coating, the bactericide is similarly dissolved in water, alcohol, or other appropriate solutions. The solution containing the bactericide is then coated on the surface of the sheets by roll coating, spray coating, or other appropriate coating methods. The coated bactericide-containing solution penetrates to the other side of the sheet and remains at both the front and ear side of the sheet.

Preferably, the solution in which the bactericide is intermixed will contain a small amount of a water soluble sizing agent, preferably 0.1% to 2% by weight. The water soluble sizing agent used may be, for example, polyvinyl alcohol, starch, carboxymethylcellulose, sodium alginate, or hydroxylpropyl cellulose.

If a bactericide is applied by immersion or coating together with a water soluble sizing agent, the bactericide will hold to the sheet surface excellently and, therefore, will not leave the oil absorbing cosmetic tissue during handling of the tissue before use. Therefore, when the consumer uses the oil absorbing cosmetic tissue, there will be sure to be enough bactericide in the oil absorbing cosmetic tissue for effective action.

The concentration of the bactericide in the solution, the amount coated, the amount impregnated, and the like can be appropriately selected so as to apply the desired amount of bactericide to the oil absorbing cosmetic tissue. If the concentrative of the solution is high, a greater amount of bactericide can be applied with the same coating amount. The reverse is true with a low concentration. The amount of bactericide applied is preferably 0.01 to 1 g, more preferably 0.05 to 0.5 g, per 1 $m^2$ oil absorbing cosmetic tissue. This should be applied evenly throughout the oil absorbing cosmetic tissue.

EXAMPLES

The present invention now will be further illustrated by, but is by no means limited to, the following Examples.

FIG. 1 shows an example of production by the immersion method. Sheet 1 of the oil absorbing cosmetic tissue is comprised of tissue having an oil-absorbing property of 15 to 25 g/$m^2$. The sheet 1 is guided by the guide roll 4 and enters the solution 6 of the bath 5. The solution 6 is a solution of 50% alcohol and 50% water by weight with the addition of methylparaben in a concentration of 5%. The sheet 1 is conveyed in the bath 5 by the immersion roll 7. When it emerges from the bath 5, it is immediately wrung out by the wringing rollers 8. Then, in the dryer 9, the sheet is dried under a blast of hot air of, for example, a temperature of 70° C. to 90° C. to produce the bactericide impregnated sheet 2. This bactericide impregnated sheet 2 is subsequently cut into the appropriate shapes and dimensions to form the oil absorbing cosmetic tissue 3. The oil absorbing cosmetic tissue 3 thus produced is packaged in piles.

On the other hand, the present oil absorbing cosmetic tissue can be produced by coating a bactericide solution is coated on the surface of the sheets.

A 0.5% by weight of carboxymethyl cellulose, 0.3% of EDTA.3Na, and 0.5% of triclosan (i.e., bactericide) are dissolved at a temperature of 60° C. to 70° C. in 68.0% of water. After allowing to cool at room temperature, 6.0% of zinc oxide, 24.0% of kaolin, 0.6% of dye, and 0.1% of perfume are added thereto, followed by treating with a homomixer. The resultnat aqueous bactericide solution was coated, at a coverage of 8 g/$m^2$, on a base sheet for the oil absorbing cosmetic tissue by using a cosmetic paper coating machine (manufactured by INOUE KINZOKU KOGYO CO., LTD.). The coated sheet was dried to fix the biocide in the resultant oil absorbing cosmetic tissue. The sheet were cut into a size of, for example, 6.5 cm × 9 cm and 100 sheets were piled and packaged as a commercial product.

In the same manner as mentioned above, another oil absorbing cosmetic tissue is produced from a bactericide solution having the following composition.

| Ingredient | % by weight |
| --- | --- |
| Water | 68.0 |
| Hydroxypropyl cellulose | 0.3 |
| Sodium hexamethaphosphate | 0.5 |
| Benzalkonium chloride | 0.5 |

| Ingredient | % by weight |
| --- | --- |
| Zinc oxide | 6.0 |
| Kaolin | 24.0 |
| Dye | 0.6 |
| Perfume | 0.1 |

According to the present invention, since a bactericide is inpregnated to oil absorbing cosmetic tissue, pressing or wiping this oil absorbing cosmetic tissue against the face kills the acne bacillus and skin staphyloccus proliferating at oily locations of the skin to suppress the proliferation of bacteria. Therefore, the amount of free fatty acids resulting from the decomposition of triglyceride by bacteria is reduced and, consequently, damage to or inflammation of skin cells by the free fatty acids can be effectively prevented.

Further, since, in the same way as with conventional oil absorbing cosmetic tissue, the sheet comprising the base of the present oil absorbing cosmetic tissue has an oil absorbing property, pressing or wiping this oil absorbing cosmetic tissue against the face removes the excess skin oil on the face, cleans the skin, and enables a better cosmetic effect.

The oil absorbing cosmetic tissue of the present invention comprises a sheet having an oil absorbing property, so can absorb excess skin oil on the face by being pressed against the face, just as with conventional oil absorbing cosmetic tissue. Further, the bactericide contained in the oil absorbing cosmetic tissue sterilizes the locations where the oil absorbing cosmetic tissue is pressed against, suppressing proliferation of bacteria. Therefore, the adverse effect of bacteria on the skin is reduced.

We claim:

1. An oil absorbing cosmetic tissue comprised of a sheet having an oil absorbing property, wherein the sheet contains a bactericide.

2. An oil absorbing cosmetic tissue according to claim 1, wherein the sheet is comprised of plant fiber.

3. An oil absorbing cosmetic tissue according to claim 1, wherein the plant fiber is hemp fiber.

4. An oil absorbing cosmetic tissue according to claim 2, wherein the sheet is comprised of a mixture of plant fiber and synthetic resin fiber.

5. An oil absorbing cosmetic tissue according to claim 1, wherein the sheet is coated with silica, talc, or other inorganic powder.

6. An oil absorbing cosmetic tissue according to claim 1, wherein the bactericide is at least one member selected from the group consisting of phenol, parachlorometacresol, resorcin, paraoxybenzoate, benzoic acid and its salts, salicylic acid and its salts, dehydroacetic acid and its salts, sorbic acid and its salts, boric acid, hexachlorophene, tetramethylthiuram disulfide, sulfur, and carbanilide bactericides.

7. An oil absorbing cosmetic tissue according to claim 1, wherein the bactericide is applied by immersion.

8. An oil absorbing cosmetic tissue according to claim 1, wherein the bactericide is applied by coating.

9. An oil absorbing cosmetic tissue according to claim 1, wherein the bactericide is applied to the sheet in a solution containing a water-soluble sizing agent.

10. An oil absorbing cosmetic tissue according to claim 8, wherein the sizing agent is contained in the solution in an amount of 0.1% to 2% by weight.

11. An oil absorbing cosmetic tissue according to claim 1, wherein the content of the bactericide is 0.01 to 1 g per 1 $m^2$ of the tissue.

12. An oil absorbing cosmetic tissue according to claim 11, wherein the content of the bactericide is 0.05 to 0.5 g.

* * * * *